United States Patent [19]
Saitou

[11] Patent Number: 5,150,254
[45] Date of Patent: Sep. 22, 1992

[54] ENDOSCOPE WITH SHAPE RECOGNITION MECHANISM

[75] Inventor: Satoshi Saitou, Tochigi, Japan

[73] Assignee: Kabushiki Kaisha Toshiba, Kawasaki, Japan

[21] Appl. No.: 513,958

[22] Filed: Apr. 24, 1990

[30] Foreign Application Priority Data

Apr. 28, 1989 [JP] Japan .................. 1-107527

[51] Int. Cl.$^5$ .................. G02B 23/00; H04N 7/18; A61B 1/06
[52] U.S. Cl. .................. 359/367; 359/740; 358/98; 128/6
[58] Field of Search .................. 350/500–522, 350/445, 318, 96.26; 128/4–8, 21, 22; 359/720–742, 888–892, 363, 367, 831, 462; 403/14, 322–327; 358/88, 98; 382/25, 37

[56] References Cited

U.S. PATENT DOCUMENTS

| | | | |
|---|---|---|---|
| 3,901,220 | 8/1975 | Koyasu et al. | 128/6 |
| 4,398,811 | 8/1983 | Nishioka et al. | 350/506 |
| 4,834,070 | 5/1989 | Saitou | 128/6 |
| 4,895,433 | 1/1990 | Takahashi et al. | 350/506 |
| 4,896,986 | 1/1990 | Tekayama | 128/4 |

FOREIGN PATENT DOCUMENTS 112216 4/1989 Japan .................. 350/130

Primary Examiner—Bruce Y. Arnold
Assistant Examiner—Thong Nguyen
Attorney, Agent, or Firm—Foley & Lardner

[57] ABSTRACT

An endoscope with a shape recognition mechanism capable of facilitating measurements with improved accuracy. In a front-viewing type, the endoscope includes a beam projection unit, to be inserted into the forceps channel, for projecting a patterned light beam to be utilized in a shape recognition on an object to be imaged by the imaging device, by which the patterned light beam is projected at a predetermined angle with respect to the object to be imaged. In a side-viewing type, the endoscope includes a beam projector part, fixed in a vicinity of the forceps outlet, for projecting a patterned light beam to be utilized in a shape recognition on an object to be imaged by the imaging device, by which the patterned light beam is projected at a predetermined angle with respect to the object to be imaged, and a beam guide part, to be inserted into the forceps channel up to a position directly underneath the beam projector parts, for guiding the source light beam to the beam projector part.

14 Claims, 8 Drawing Sheets

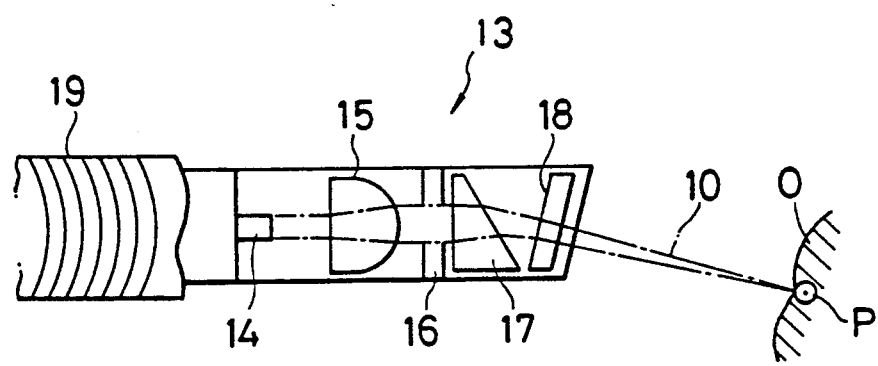
FIG.6
FIG.7 FIG.8 FIG.9
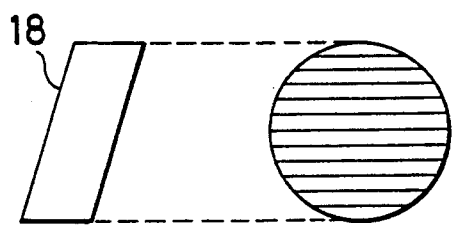 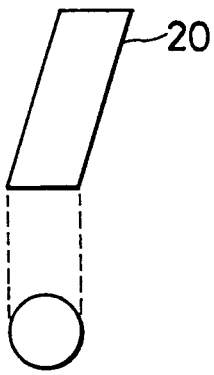 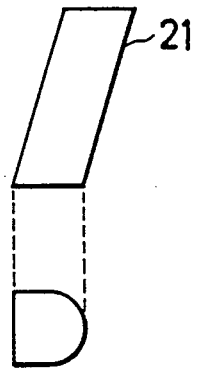
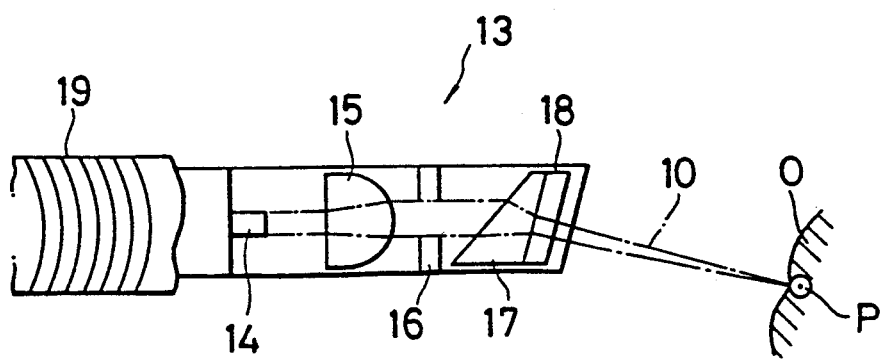
FIG.10

ENDOSCOPE WITH SHAPE RECOGNITION MECHANISM

BACKGROUND OF THE INVENTION

1. Field of the Invention

The present invention relates to an endoscope equipped with a shape recognition mechanism for facilitating the measurement of a shape of an object to be examined.

2. Description of the Background Art

Recently, there have been many propositions for an endoscope equipped with a shape recognition mechanism for facilitating the measurement of the shape of an object to be examined by projecting a patterned beam onto a surface of the object such that a pattern for facilitating the measurement is superposed on an image of the object taken by an imaging device of the endoscope.

A conventional endoscope equipped with the shape recognition mechanism operates as follows.

Namely, as shown in FIG. 1 for a front-viewing type endoscope, a patterned laser beam 102 is projected upon an object to be examined 103 from a beam projection unit 106 inserted into a forceps channel 107 located on a scope end surface of the scope 101, so that a line shaped pattern 104 is formed on the object 103. A reflection of the line shaped pattern 104 is then imaged by an imaging device 105 also located on the scope end surface of the scope 101 at a location separated from the forceps channel 107, along with an image of the object 103, so that the image of the object 103 with the pattern 104 superposed can be obtained. A shape of the object 103 is then analyzed on a basis of such an image with the pattern 104 superposed.

Here, as shown in FIG. 2, when a projection angle of the patterned laser beam 102 is $\theta_P$, a receiving angle of the reflection of the pattern 104 is $\theta_R$, a parallax Pa is given by a distance between a projection position of the patterned laser beam 102 and a center of the imaging device 105, and a length of the beam projection unit 106 protruding from the scope end surface of the scope 101 is d, a coordinate $(X_P, Y_P, Z_P)$ of the pattern 104 with respect to an origin located at the center of the imaging device 105 can be expressed by:

$Z_P = (Pa + d \cdot \tan \theta_P)/(\tan \theta_P + \tan \theta_R)$ $X_P = Z_P \cdot \tan \theta_R$ $Y_P = Z_P \cdot \tan \theta_Y$ where $\theta_Y$ is a receiving angle of the reflection of the pattern 104 with respect to a Y axis.

Now, such a conventional front-viewing type endoscope with a shape recognition mechanism is known to be associated with the following problems.

First of all, when the beam projection unit is provided as a permanent additional feature to an ordinary endoscope, a diameter of the scope becomes too large for practical use.

For this reason, the beam projection unit is usually inserted into the forceps channel of an ordinary endoscope as in the example of FIG. 1. However, in a conventional endoscope with a shape recognition mechanism, a position of the beam projection unit in the forceps channel could not be fixed, so that the length d and the projection angle $\theta_P$ in the above expressions could not be specified with a sufficient accuracy, which in turn affects the accuracy of the measurement of the shape.

Secondly, as shown in FIGS. 3(A) and (B), with the beam projection unit 106 inserted into the forceps channel 107, the length d and the projection angle $\theta_P$ are changed depending on a degree and a direction of bending of the scope 101, which also contributed to the inaccuracy of the measurement of the shape.

On the other hand, there is a side-viewing type endoscope with a shape recognition mechanism. In such a side-viewing type endoscope, the parallax is not limited by a size of the scope end surface of the scope, so that an accuracy of the measurment can be improved.

However, the problems described above for the front-viewing type endoscope are also pertinent for the side-viewing type endoscope.

SUMMARY OF THE INVENTION

It is therefore an object of the present invention to provide an endoscope with a shape recognition mechanism capable of facilitating a measurement of improved accuracy by stabilizing the projection angle and the projection position of the patterned beam.

According to one aspect of the present invention there is provided a front-viewing type endoscope, comprising: a scope section having a forceps channel opening to a scope end surface and an imaging device located on the scope end surface; and beam projection means, to be inserted into the forceps channel, for projecting a patterned light beam to be utilized in a shape recognition on an object to be imaged by the imaging device, the beam projection means including: means for generating the patterned light beam from a source light beam such that the patterned light beam is projected at a predetermined angle with respect to the object to be imaged; prism means for deflecting the source light beam such that the source light beam enters the generating means at a right angle; diaphragm means for controlling an amount of the source light beam entering the prism means; lens means for focusing the source light beam entering the collimator means; and light guide means for transmitting the source light beam to the lens means.

According to another aspect of the present invention there is provided a side-viewing type endoscope, comprising: a scope section having a forceps channel having a forceps outlet opening to a side of a scope end portion and an imaging device located on the scope end portion; beam projector means, fixed in a vicinity of the forceps outlet, for projecting a patterned light beam to be utilized in a shape recognition on an object to be imaged by the imaging device, the beam projector means including: means for generating the patterned light beam from a source light beam such that the patterned light beam is projected at a predetermined angle with respect to the object to be imaged; and prism means for deflecting the source light beam such that the source light beam enters the generating means at a right angle; and beam guide means, to be inserted into the forceps channel up to a position directly underneath the beam projector means, for guiding the source light beam to the beam projector means, the beam guide means including: beam deflection means for deflecting the source light beam toward the prism means of the beam projector means; collimator means for controlling an amount of the source light beam entering the beam deflecting means; lens means for focusing the source light beam entering the collimator means; and light guide means for transmitting the source light beam to the lens means.

Other features and advantages of the present invention will become apparent from the following description taken in conjunction with the accompanying drawings.

BRIEF DESCRIPTION OF THE DRAWINGS

FIG. 6 is a detailed cross sectional view of another possible configuration for a scope end portion of the endoscope system of FIG. 4.

FIG. 7 is a cross sectional view accompanied by a front view of a diffraction grating that may be utilized in the configuration shown in FIG. 6.

FIG. 8 is a cross sectional view accompanied by a top plan view of a rod lens that may be utilized in the configuration shown in FIG. 6.

FIG. 9 is a cross sectional view accompanied by a top plan view of a cylindrical lens that may be utilized in the configuration shown in FIG. 6.

FIG. 10 is a detailed cross sectional view of another possible configuration for a scope end portion of the endoscope system of FIG. 4.

DETAILED DESCRIPTION OF THE PREFERRED EMBODIMENTS

Figure 1:
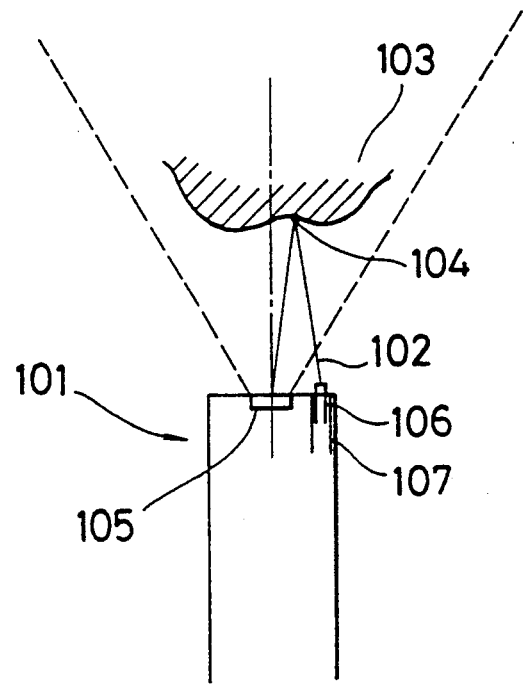
FIG. 1 is a schematic diagram of a scope end portion of a conventional endoscope equipped with a shape recognition mechanism.
Figure 2:
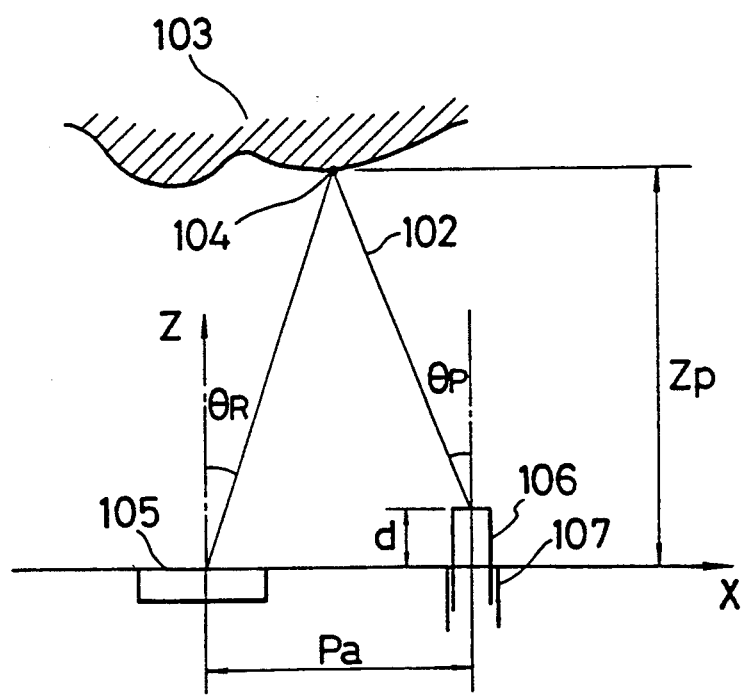
FIG. 2 is a diagram for explaining an operation of the conventional endoscope of FIG. 1.
Figure 3A:
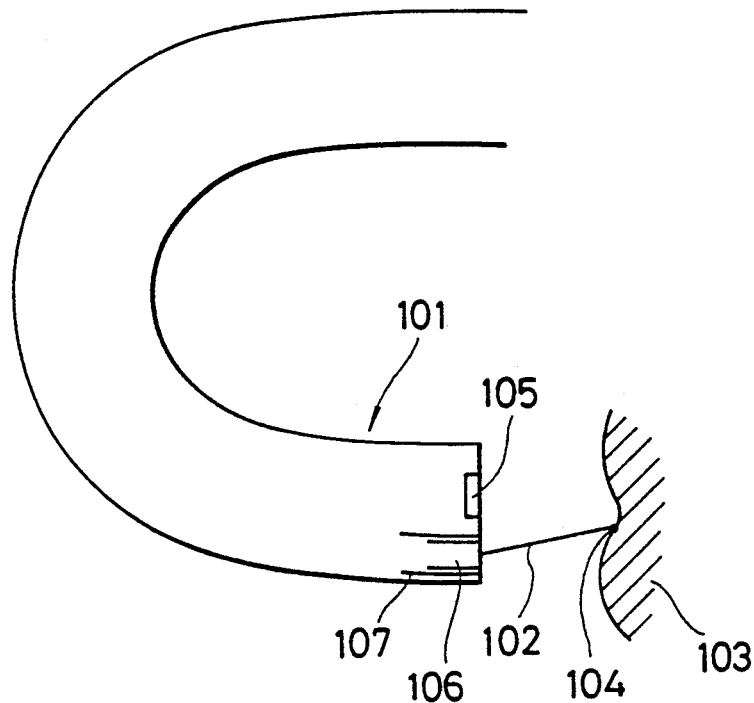
FIGS. 3(A) and (B) are schematic diagrams of a scope end portion of a conventional endoscope equipped with a shape recognition mechanism for explaining a problem associated with it.
Figure 3B:
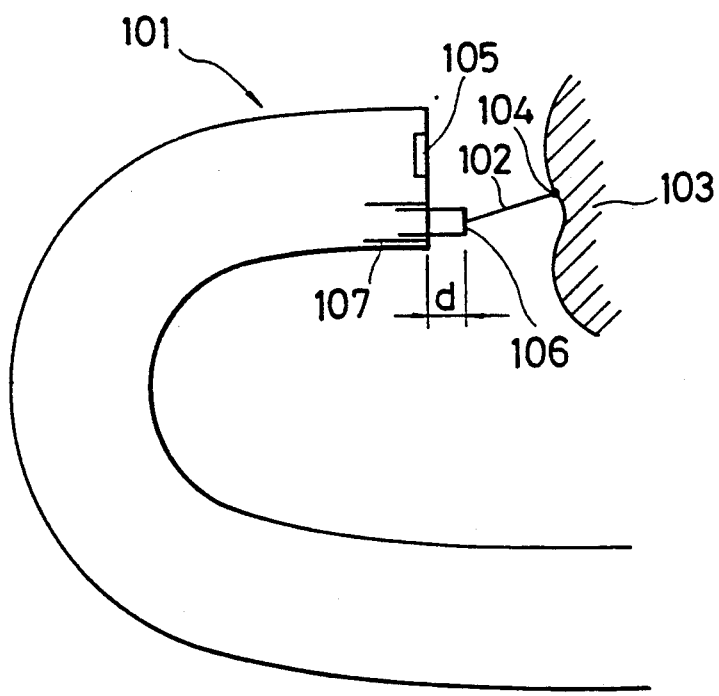
Figure 4:
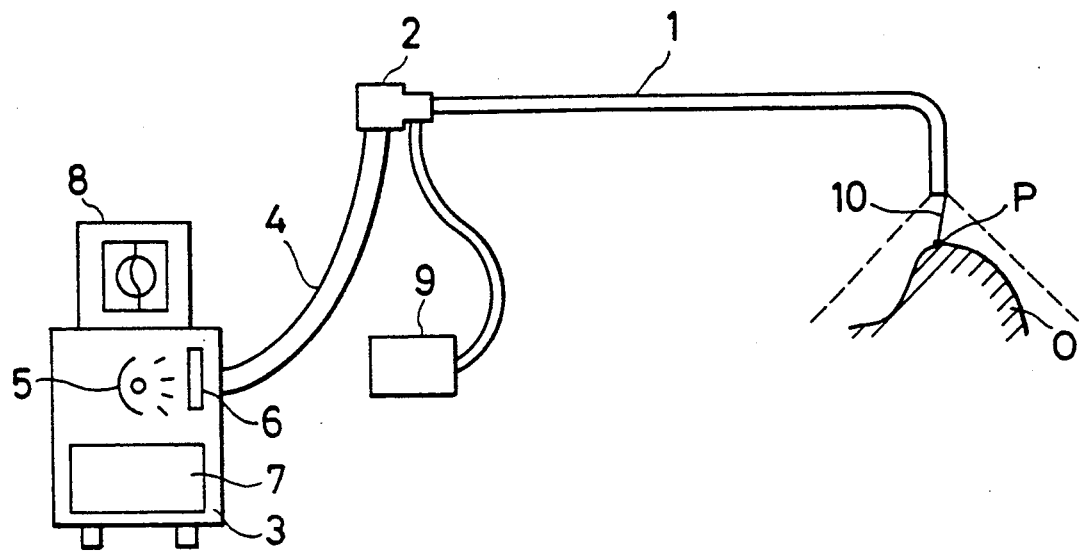
FIG. 4 is a schematic block diagram for one embodiment of an endoscope system with a shape recognition mechanism in a form of a front-viewing type endoscope according to the present invention.

Referring now to FIG. 4, there is shown one embodiment of a front-viewing type endoscope system with a shape recognition mechanism according to the present invention.

In this embodiment, the endoscope system comprises a scope section 1 including a scope grip section 2, a system body 3, connected with the scope section by a joint cord 4, including a light source 5 for providing a light to illuminate an object 0 to be imaged, which is transmitted through a light guide (not shown) provided in the scope section 1 and the joint cord 4, a rotary filter 6 for selectively switching the light from the light source 5 on and off, and an image processor 7 for processing an image taken by the scope section 1, a monitor 8 for displaying the image processed by the image processor 7, and a laser source 9 for providing a laser beam for generating a patterned laser beam 10 to be projected onto the object 0 in order to make a pattern P on the object 0.

Figure 5:
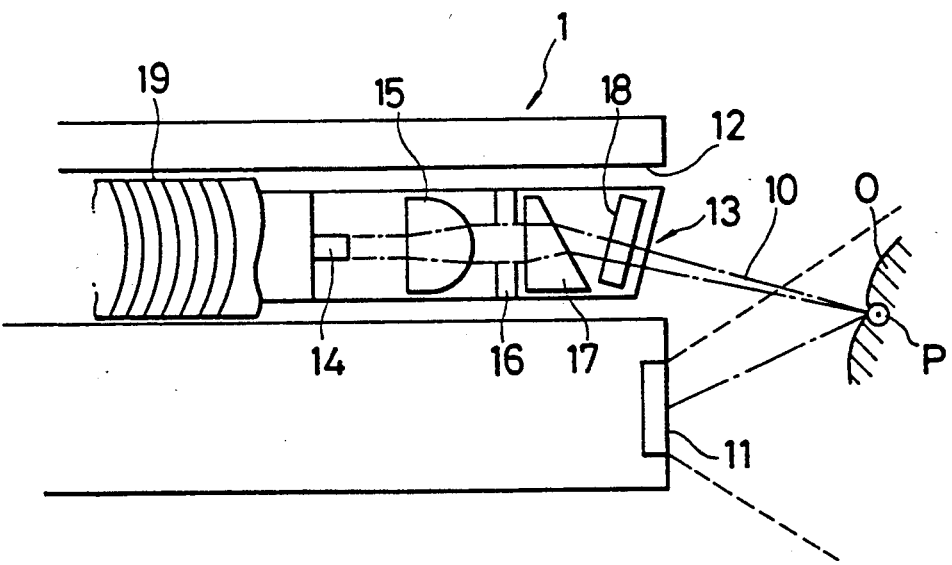
FIG. 5 is a detailed cross sectional view of one possible configuration for a scope end portion of the endoscope system of FIG. 4.

As shown in FIG. 5, a scope end portion of the scope section 1 has an imaging device 11 for taking images of the object 0, and a forceps channel 12 ordinarily utilized for inserting a forceps to be used in conjunction with the endoscope system.

In this embodiment, when the shape recognition mechanism is to be used, a beam projection unit 13 for projecting the patterned laser beam is inserted into the forceps channel 12.

The beam projection unit 13 comprises an optical fiber 14 for transmitting the laser beam from the laser source 9, a focusing lens 15 for focusing the laser beam transmitted through the optical fiber 14, a diaphragm 16 for adjusting an amount of laser beam focused by the focusing lens 15, a prism 17 for deflecting the laser beam passing through the diaphragm 16, and a diffraction grating 18 for producing the patterned laser beam 10 from the laser beam deflected by the prism 17.

In this beam projection unit 13, the prism 17 for deflecting the laser beam is used in order to place the pattern P at a center of an image taken by the imaging device 11. Namely, it is usually preferable to bring the imaging device 11 to about 20 to 30 mm away from the object 0, and at such a position of the imaging device 11, the patterned laser beam 10 needs to be projected at an angle of about 10° to 20° in order to place the pattern P at a center of an image taken by the imaging device 11. Unless the patterned laser beam 10 is projected at that angle, a straight line shaped pattern P is known to appear in an image taken by the imaging device 11 as a curved line.

Also, the focusing lens 15 preferably has a focal length within a range of 2.5 mm to 4.0 mm. This is because in order to focus the laser beam from the optical fiber 14 on the object 0, a focal length of more than 2.5 mm is desirable, while the focal length of the focusing lens cannot be made too large because of a limitation due to a size of the beam projection unit 13, so that the focal length of less than 4.0 mm is desirable.

This beam projection unit 13 is covered by a so called torque cable 19. The torque cable is a cylindrical tube like cable of approximately 2.0 to 2.5 mm diameter formed by winding stainless wires of approximately 0.5 mm diameter in a manner of a coil, which possesses a property that when one end of the torque cable is rotated by a certain amount of angle, the other end of the torque cable also rotates by the same amount of angle. Thus, a front end of the beam projection unit 13 located at the scope end surface of the scope 1 can be rotated by rotating a rear end of the beam projection unit 13 located at a forceps insertion port (not shown) located near the scope grip portion 2.

Now, as can be seen in FIG. 5, the diffraction grating 18 must be tilted such that the laser beam deflected by the prism 17 enters the diffraction grating 18 at a right angle. This feature is important for making a line shaped pattern P as straight as possible.

Here, as shown in FIG. 6, instead of tilting the diffraction grating 18 having a rectangular cross sectional shape as in FIG. 5, the diffraction grating 18 having a rhomboidal cross sectional shape which is provided at the end of the beam projection unit 13 with a predetermined angle with respect to the scope end portion such as that shown in FIG. 7 may be used, for the sake of easy and stable installation of the diffraction grating 18. Similarly, the diffraction grating 18 may be replaced by a rod lens 20 shown in FIG. 8 or a cylindrical lens 21 shown in FIG. 9, both of which are similarly shaped into rhomboidal cross sectional shapes.

Figure 11:
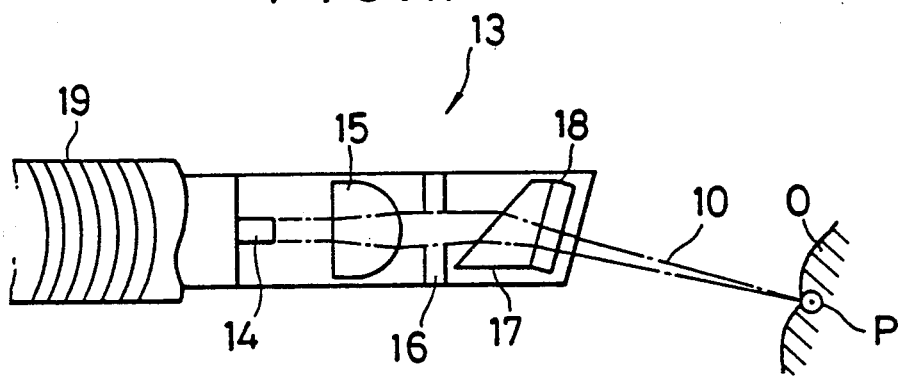
FIG. 11 is a detailed cross sectional view of another possible configuration for a scope end portion of the endoscope system of FIG. 4.

Furthermore, as shown in FIGS. 10 and 11, the prism 17 may be shaped differently from that shown in FIGS. 5 and 6 such that the prism 17 and the diffraction grating 18 can be placed adjacent each other in direct contact.

Figure 12:
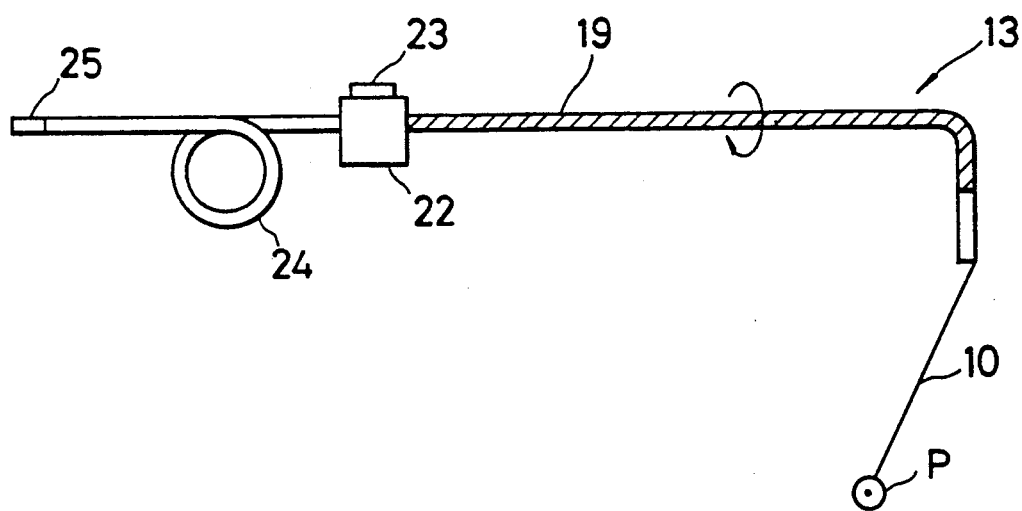
FIG. 12 is a side view of a beam projection unit of the endoscope system of FIG. 4.

The beam projection unit 13 is shown in its entirety in FIG. 12. As shown in FIG. 12, the beam projection unit 13 covered by the torque cable 19 shown in FIG. 5 is further equipped with an adjusting member 22 having a key 23, a connecting tube 24, and a photo connector 25 to be connected to the laser source 9.

Figures 13, 14:
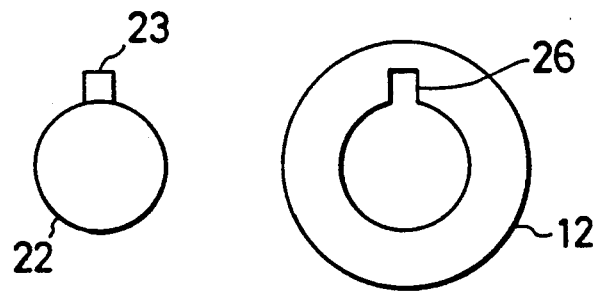
FIG. 13 is a cross sectional view of an adjusting member of the beam projection unit of FIG. 12.
FIG. 14 is a cross sectional view of one end of a forceps channel of the endoscope system of FIG. 4.

The adjusting member 22 has a circular cross section with the key 23 mounted on top as shown in FIG. 13, and the key 23 is to be engaged with a key groove 26 provided on the forceps channel 12 as shown in FIG. 14. By means of this engagement of the key 23 and the key groove 26, the projection angle of the patterned laser beam can be fixed accurately at a predetermined appropriate angle.

Here, when the beam projection unit 13 is inserted into the forceps channel 12 initially, an operator is only required to turn the beam projection unit 13 at the adjusting member 22 so as to engage the key 23 with the key groove 26. Then, because of the torque cable 19, a front end portion of the beam projection unit 13 shown in FIG. 5 also rotates by the same angle as the adjusting member 22 is turned by the operator.

This endoscope system with a shape recognition mechanism operates as follows.

Namely, the patterned laser beam 10 is projected upon the object 0 from the beam projection unit 13 inserted into the forceps channel 12 located on the scope end surface of the scope 1, so that a line shaped pattern P is formed on the object 10. A reflection of the line shaped pattern P is then imaged by the imaging device 11 also located on the scope end surface of the scope 1 at a location separated from the forceps channel 12, along with an image of the object 0, so that the image of the object 0 with the pattern P superposed can be obtained. The image so obtained by the imaging device 11 is displayed on a display screen 27 of the monitor 8 as shown in FIG. 15, so that a shape of the object 0 can then be analyzed on a basis of such an image with the pattern P superposed.

Figure 15:
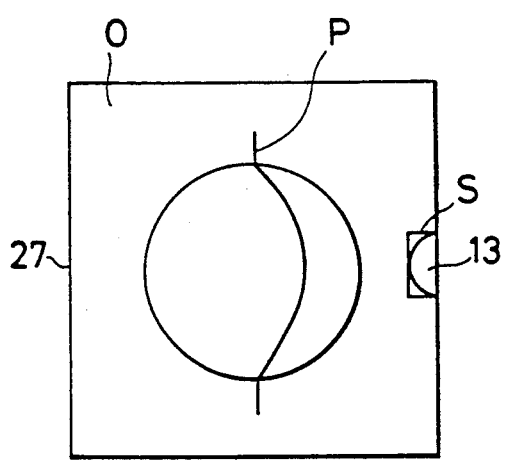
FIG. 15 is an illustration of an example of display obtained by the endoscope system of FIG. 4.

Here, in order to place the beam projection unit 13 at a predetermined appropriate projection position, a specific region S is provided on the display screen 27 of the monitor 8, as shown in FIG. 15, and the operator gradually inserts the beam projection unit 13 until a head of the beam projection unit 13 is fit in this specified region S. By means of this provision, the projection position of the patterned laser beam can be fixed accurately to a predetermined appropriate position.

Figure 16:
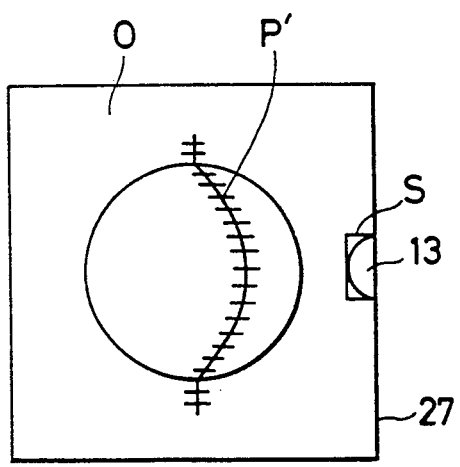
FIG. 16 is an illustration of another example of display obtained by the endoscope system of FIG. 4.

Instead of the line shaped pattern P shown in FIG. 15, a scale marking pattern P' shown in FIG. 16 may be superposed on the image of the object 0.

In addition to the stabilization of the projection position and the projection angle, according to this embodiment, the beam projection unit 13 is inserted into the forceps channel 12 only when the measurement utilizing the shape recognition mechanism is desired, and otherwise the forceps channel 12 can be utilized to operate the forceps as in a usual endoscope, so that there is no need to prepare separate endoscopes for the usual operation and the operation utilizing the shape recognition mechanism.

Now, another embodiment in a form of a side-viewing type endoscope system with a shape recognition mechanism according to the present invention will be described.

Here, the endoscope system in general is similar to that shown in FIG. 4 for the previous embodiment, except for a detail of a front end portion of the scope.

In this case of a side-viewing type, rather than inserting an entire beam projection unit into the forceps channel as in the previous embodiment of a front-viewing type, the beam projection unit is divided into a beam projector part to be fixed in a vicinity of the forceps outlet, and a beam guide part to be inserted into the forceps channel.

Figure 17:
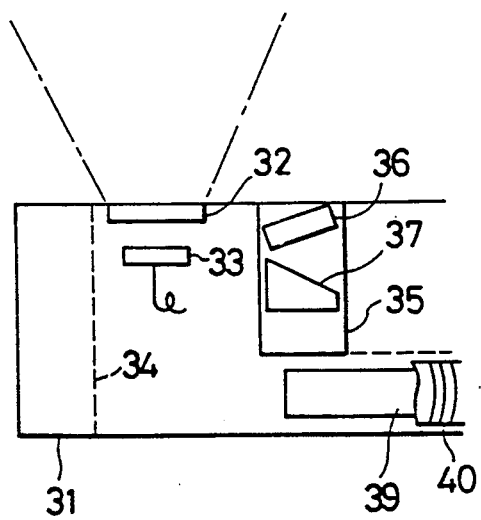
FIG. 17 is a detailed cross sectional view of one possible configuration for a scope end portion of another embodiment of the endoscope system in a form of a side-viewing type endoscope according to the present invention.

Thus, as shown in FIG. 17, in this embodiment, an end portion of the scope section 31 has an observation window 32, an imaging device 33, located underneath the observation window 32, for taking images of an object to be imaged, and a forceps channel having a forceps outlet 34 pointing sideways which is ordinarily utilized for inserting a forceps to be used in conjunction with the endoscope system. The observation window 32 is located next to the forceps outlet 34 with a prescribed separation, as shown in FIG. 18.

Figure 18:
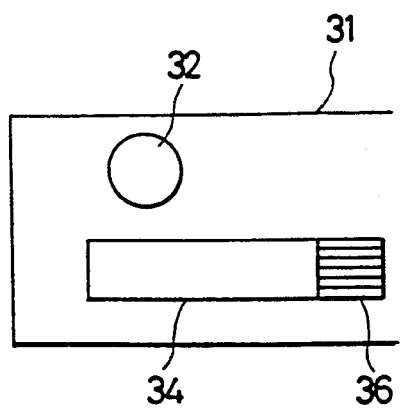
FIG. 18 is an enlarged side view of a scope end portion of the embodiment of the endoscope system shown in FIG. 17.

In addition, in a vicinity of the forceps outlet 34, preferably adjacent to the forceps outlet 34 and as far away from the observation window 32 as possible as in FIG. 18, the beam projector part 35 of the beam projection unit is fixed, such that when the beam guide part 39 of the beam projection unit equipped with a torque cable 40 is inserted into the forceps channel for a sufficient amount, a laser beam transmitted through the beam guide part 39 can be directed into the beam projector part 35. The provision of placing the beam projector part 35 adjacent to the forceps outlet 34 and as far away from the observation window 32 as possible is for obtaining as large a parallax as possible.

The beam projector part 35 comprises a diffraction grating 36 for producing the patterned laser beam, and a prism 37 for deflecting the laser beam entering the beam projector part 35 to direct toward the diffraction grating at a right angle.

As in the previous embodiment, the prism 37 for deflecting the laser beam is used in order to place the pattern P at a center of an image taken by the imaging device 33. Namely, as already mentioned in conjunction with the previous embodiment, it is usually preferable to bring the imaging device 33 to about 20 to 30 mm away from the object, and at such a position of the imaging device 33, the patterned laser beam needs to be projected at an angle of about 10° to 20° in order to place the pattern P at a center of an image taken by the imaging device 33. Unless the patterned laser beam is projected at that angle, a straight line shaped pattern P is known to appear in an image taken by the imaging device 33 as a curved line.

Figure 19:
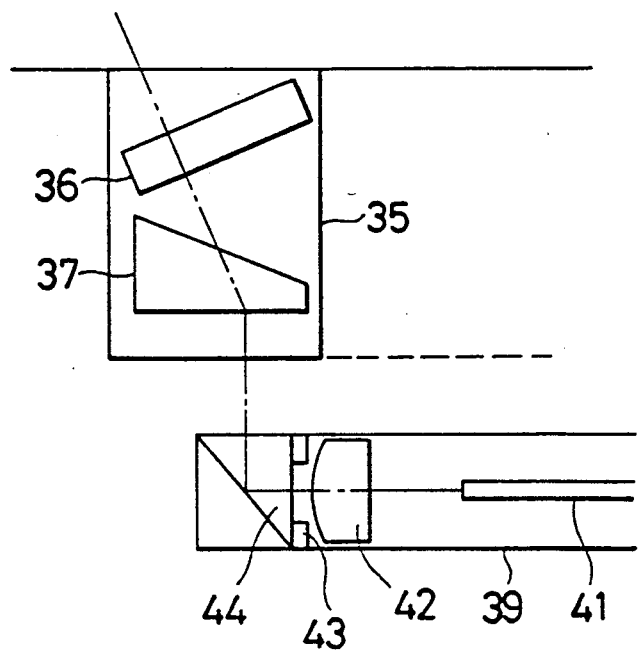
FIG. 19 is a detailed cross sectional view of one possible configuration for a beam projector part and the beam guide part in a scope end portion of FIG. 17.

The beam guide part 39 comprises, as shown in FIG. 19, an optical fiber 41 for transmitting the laser beam from a laser source of the endoscope system, a focusing lens 42 for focusing the laser beam transmitted through the optical fiber 41, a diaphragm 43 for adjusting an amount of laser beam focused by the focusing lens 42, and a triangular prism 44 for deflecting the laser beam from the optical fiber 41 at a right angle so as to direct the laser beam toward the beam projector part 35.

Here, as in the previous embodiment, the focusing lens 42 preferably has a focal length within a range of 2.5 mm to 4.0 mm for the same reason as already mentioned in conjunction with the previous embodiment.

Also, the torque cable 40 is used to cover the beam guide part 39. This torque cable is similar to that used in the previous embodiment. Thus, a front end of the beam guide part 39 located underneath the beam projector part 35 can be rotated by rotating a rear end of the beam guide part 39 located at a forceps insertion port (not shown) located near a scope grip portion of the scope.

Also, similarly to the previous embodiment, the diffraction grating 36 must be tilted such that the laser beam deflected by the prism 37 enters the diffraction grating 36 at a right angle. This feature, as already mentioned, is important for making a line shaped pattern P as straight as possible.

Figure 20:
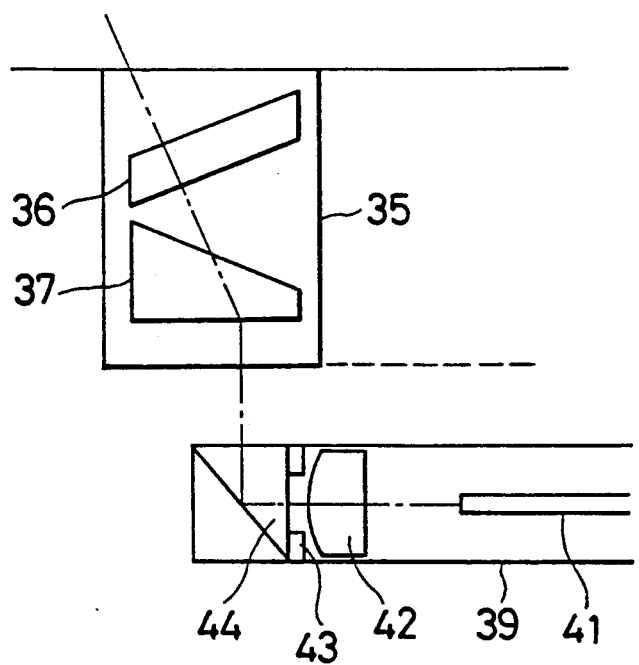
FIG. 20 is a detailed cross sectional view of another possible configuration for a beam projector part and the beam guide part in a scope end portion of FIG. 17.

As shown in FIG. 20, instead of tilting the diffraction grating 36 having a rectangular cross sectional shape, the diffraction grating 36 having a rhomboidal cross sectional shape which is provided at an end of the beam projector part 35 with a predetermined angle with respect to the scope end portion may be used, for the sake of easy and stable installation of the diffraction grating 36. As in the previous embodiment, the diffraction grating 36 may be replaced by a rod lens or a cylindrical lens which is similarly shaped into a rhomboidal cross sectional shape.

Figure 21:
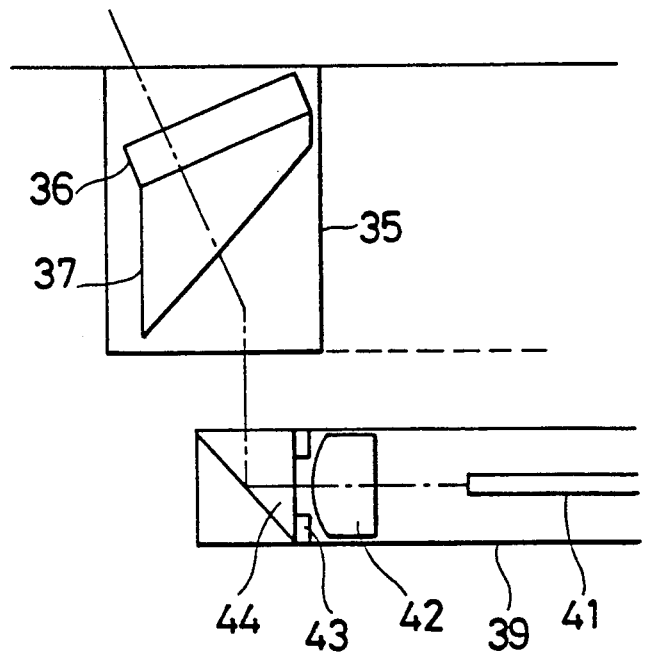
FIG. 21 is a detailed cross sectional view of another possible configuration for a beam projector part and the beam guide part in a scope end portion of FIG. 17.
Figure 22:
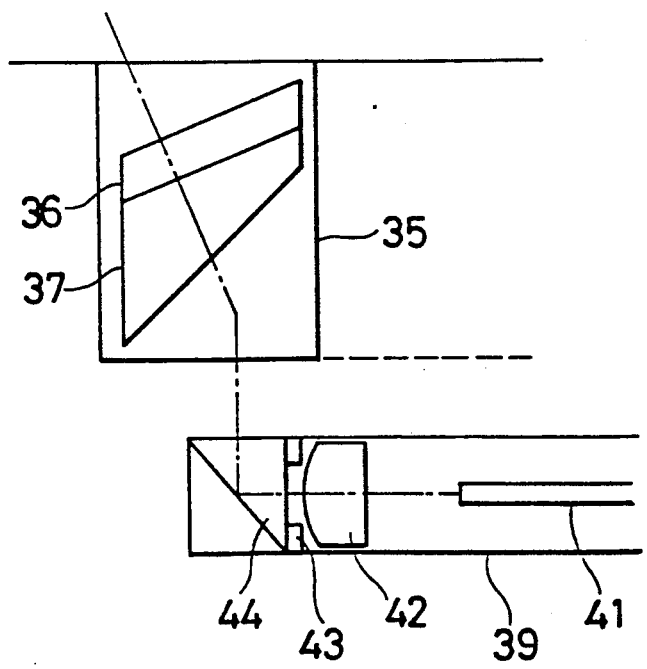
FIG. 22 is a detailed cross sectional view of another possible configuration for a beam projector part and the beam guide part in a scope end portion of FIG. 17.

Furthermore, as in the previous embodiment, as shown in FIGS. 21 and 22, the prism 37 may be shaped differently from that shown in FIGS. 19 and 20 such that the prism 37 and the diffraction grating 36 can be placed adjacent to each other in direct contact.

Also, as in the previous embodiment, the beam guide part 39 is further equipped with an adjusting member having a key to be engaged with a key groove provided on the forceps channel. By means of this engagement of the key and the key groove, the projection angle of the patterned laser beam can be fixed accurately at a predetermined appropriate angle.

Here, when the beam guide part 39 is inserted into the forceps channel 12 initially, an operator is only required to turn the beam guide part 39 at the adjusting member so as to engage the key with the key groove. Then, because of the torque cable 40, a front end portion of the beam guide part 39 also rotates by the same angle as the adjusting member is turned by the operator.

Thus, this endoscope system with a shape recognition mechanism operates as follows.

Namely, the patterned laser beam is projected upon the object from the beam guide part 39 inserted into the forceps channel through the beam projector part 35 fixed in a vicinity of the forceps outlet 34, so that a line shaped pattern is formed on the object. A reflection of the line shaped pattern is then imaged by the imaging device 33 through the observation window 32, along with an image of the object, so that the image of the object with the pattern superposed can be obtained. The image so obtained by the imaging device 33 is displayed on a display screen of a monitor, so that a shape of the object can then be analyzed on a basis of such an image with the pattern superposed.

As described, according to the side-viewing type endoscope of this embodiment, the projection position of the patterned laser beam can be fixed accurately to a predetermined appropriate position, because the beam projector part 35 is rigidly fixed in a vicinity of the forceps channel.

Moreover, according to this embodiment, the beam guide part 39 is inserted into the forceps channel only when the measurement utilizing the shape recognition mechanism is desired, and otherwise the forceps channel can be utilized to operate the forceps as in a usual endoscope, so that there is no need to prepare separate endoscopes for the usual operation and the operation utilizing the shape recognition mechanism.

It is to be noted that a location of the beam projector part 35 is not restricted to that shown in FIGS. 17 and 18, so long as it can be placed directly above the beam guide part 39 inserted through the forceps channel and avoid obstructing the operation using the forceps in the usual operation.

It is also to be noted that the triangular prism 44 of the beam guide part 39 may be replaced by a mirror tilted at 45°.

Besides these, many modifications and variations of the above embodiments may be made without departing from the novel and advantageous features of the present invention. Accordingly, all such modifications and variations are intended to be included within the scope of the appended claims.

What is claimed is:

1. A front-viewing type endoscope, comprising:
a scope section in a cable having a forceps channel opening to a scope end surface and an imaging device located on the scope end surface; and
beam projector means to be inserted into the forceps channel for projecting a patterned light beam for shape recognition of an object to be imaged by the imaging device, the beam projector means including:
means for generating the patterned light beam from a source light beam such that the patterned light beam is projected at a predetermined angle with respect to the object to be imaged;
prism means for deflecting the source light beam such that the source light beam prependicularly enters the generating means;
diaphragm means for controlling an amount of the source light beam entering the prism means;

lens means for focusing the source light beam entering the diaphragm means; and light guide means for transmitting the source light beam to the lens means.

2. The endoscope of claim 1, further comprising a torque cable means, which is capable of rotating one end of the cable by an identical angle as the other end is rotated, the cable covering the beam projector means.

3. The endoscope of claim 2, wherein the forceps channel contains a key groove on a portion of the forceps channel away from the scope end surface, and the torque cable means is equipped with an adjusting member having a key to be engaged with the key groove, such that the angle of projection of the patterned light beam is fixed at a predetermined angle when the key is engaged with the key groove.

4. The endoscope of claim 1, wherein the generating means is one of a diffraction grating, rod lens, or cylindrical lens, which is shaped to have a rhomboidal cross sectional shape, and which is positioned at an end of the beam projector means with the predetermined angle with respect to the scope end surface.

5. The endoscope of claim 4, wherein the generating means and the prism means directly contact each other in the beam projector means.

6. The endoscope of claim 1, wherein the lens means has a focal length within a range of 2.5 to 4.0 mm.

7. The endoscope of claim 1, wherein the beam projector means is inserted into the forceps channel to such an extent that a prescribed length of the beam projector means enters into a view field of the imaging device.

8. A side-viewing type endoscope, comprising:

a scope section within a cable having a forceps channel with a forceps outlet opening to a side of a scope end portion and an imaging device located in the scope end portion;

beam projector means, fixed in the vicinity of the forceps outlet, for projecting a patterned light beam for the shape recognition of an object to be imaged by the imaging device, the beam projector means including:

means for generating the patterned light beam from a source light beam such that the patterned light beam is projected at a predetermined angle with respect to the object to be imaged;

prism means for deflecting the source light beam such that the source light beam perpendicularly enters the generating means; and beam guide means inserted into the forceps channel up to a position directly underneath the beam projector means, for guiding the source light beam to the beam projector means, the beam guide means including:

beam deflection means for deflecting the source light beam toward the prism means of the beam projector means;

diaphragm means for controlling an amount of the source light beam entering the beam deflection means;

lens means for focusing the source light beam entering the diaphragm means; and light guide means for transmitting the source light beam to the lens means.

9. The endoscope of claim 8, further comprising a torque cable means, which is capable of rotating one end of the cable by an identical angle as the other end is rotated, the cable covering the beam projector means.

10. The endoscope of claim 9, wherein the forceps channel has a key groove on a portion of the forceps channel away from the scope end portion, and the torque cable means is equipped with an adjusting member having a key to be engaged with the key groove, such that the angle of projection of the patterned light beam is fixed at a predetermined angle when the key is engaged with the key groove.

11. The endoscope of claim 8, wherein the generating means is one of a diffraction grating, rod lens, or cylindrical lens, which is shaped to have a rhomboidal cross sectional shape, and which is provided at an end of the beam projector means with the predetermined angle with respect to the scope end portion.

12. The endoscope of claim 11, wherein the generating means and the prism means directly contact each other in the beam projector means.

13. The endoscope of claim 8, wherein the lens means has a focal length within a range of 2.5 to 4.0 mm.

14. The endoscope of claim 8, wherein the beam projector means is located at a position immediately adjacent to the forceps outlet, at which a separation between the imaging device and the beam projector means is maximum among all positions immediately adjacent to the forceps outlet.

* * * * *